United States Patent
Hood

(10) Patent No.: US 11,607,053 B2
(45) Date of Patent: Mar. 21, 2023

(54) BED FRAME SYSTEM

(71) Applicant: Happy Ferret Innovations LLC, Dallas, TX (US)

(72) Inventor: Amy Hood, Dallas, TX (US)

( * ) Notice: Subject to any disclaimer, the term of this patent is extended or adjusted under 35 U.S.C. 154(b) by 683 days.

(21) Appl. No.: 16/660,098

(22) Filed: Oct. 22, 2019

(65) Prior Publication Data

US 2020/0146461 A1 May 14, 2020

Related U.S. Application Data

(60) Provisional application No. 62/767,494, filed on Nov. 14, 2018.

(51) Int. Cl.
*A47C 19/00* (2006.01)
*A47C 21/00* (2006.01)
*A61M 21/02* (2006.01)
*A61M 21/00* (2006.01)

(52) U.S. Cl.
CPC ............ *A47C 21/006* (2013.01); *A47C 19/00* (2013.01); *A61M 21/02* (2013.01); *A61M 2021/0022* (2013.01); *A61M 2205/33* (2013.01)

(58) Field of Classification Search
CPC ....... A47C 21/00; A47C 21/006; A47C 19/00; A61M 21/00; A61M 21/02; A61M 2021/0022; A61M 2205/33
See application file for complete search history.

(56) References Cited

U.S. PATENT DOCUMENTS

2014/0250592 A1    9/2014  Karp et al.
2017/0318978 A1*  11/2017  Flemister ............. A61G 11/008

FOREIGN PATENT DOCUMENTS

CN          2781931        5/2006
CN          106235762      12/2016

OTHER PUBLICATIONS

International Search Report and Written Opinion, dated Jan. 14, 2020, for PCT/US19/57635.

* cited by examiner

*Primary Examiner* — Fredrick C Conley

(57) ABSTRACT

A bed frame system and a movable frame may simulate movement of a body of water. The bed frame system and the movable frame may improve sleep and sleep patterns of a user and may provide additional health benefits. An intensity of movement of the bed frame system and the movable frame may be controlled by utilizing a controller and/or a mobile application. A predetermined time period of movement may also be controlled by utilizing a controller and/or a mobile application.

8 Claims, 1 Drawing Sheet

100

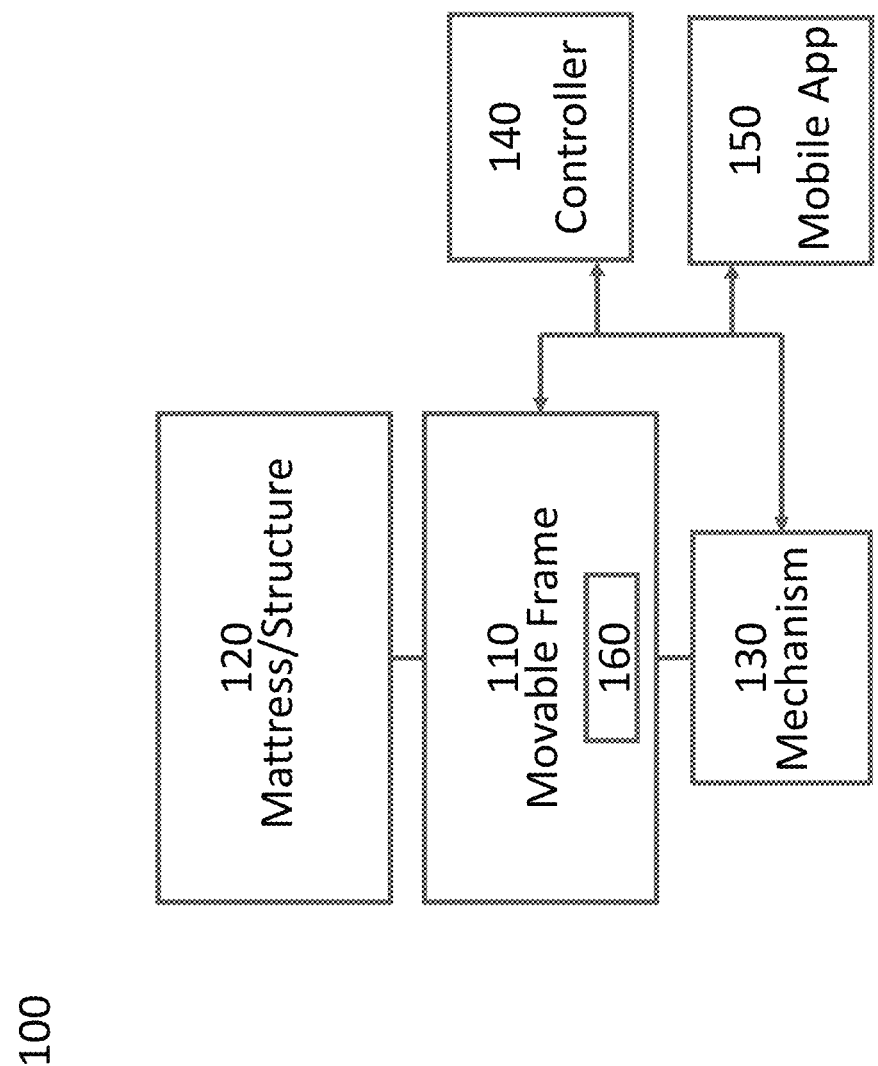

BED FRAME SYSTEM

CROSS-REFERENCE TO RELATED APPLICATION

The present application claims priority under 35 U.S.C. 119(e) to U.S. Provisional Application No. 62/767,494, filed Nov. 14, 2018, which is incorporated by reference in its entirety.

TECHNICAL FIELD

The disclosure relates generally to a bed frame system. In particular, the disclosure relates to a bed frame system that may simulate or mimic the movement of a body of water.

BACKGROUND

Generally, bed frames can support a mattress and may even support a movable mattress. Additionally, bed frames can be adjustable or controlled by hydraulics to assume a position that can satisfy user needs and/or preferences. While bed frames can be adjustable, they typically hold a static position after being adjusted by the user.

SUMMARY

Embodiments of the present disclosure generally provide a bed frame system and a movable frame that may simulate or mimic the movement of a body of water. The bed frame system may create a rhythmic motion in some embodiments of the present disclosure. The bed frame system and the movable frame may improve user sleep and/or sleep patterns.

Embodiments of the present disclosure may provide a bed frame system that may include a movable frame that may be arranged to support a mattress provided on a top of the movable frame. The bed frame system may further include a mechanism that may be attached underneath the movable frame. The mechanism may be arranged to move the movable frame in an oscillatory motion similar to a motion of a body of water. The bed frame system may provide a controller that may be configured to adjust an intensity of the movement that may be caused by the mechanism. The controller may be configured to adjust a time period that the movable frame and the mattress move. A mobile application may be in communication with the bed frame system and may adjust the intensity of the movement that may be caused by the mechanism. The mobile application may also adjust the time period that the movable frame and the mattress move. The bed frame system may include an electronic system that may be arranged in a housing attached to the movable frame. A ball and socket may be arranged to move the movable frame and the mattress. A plurality of legs may be attached to the frame and may stabilize the bed on top of the movable frame. At least one additional leg, in addition to the plurality of legs, may be arranged to provide greater support for the bed frame system.

Other embodiments of the present disclosure may provide a movable frame that may provide a structure that may be made of a deformable material placed on a top of the movable frame. An electronic mechanism may be attached underneath the movable frame and may create a movement of the movable frame that may mimic a motion of a body of water. A plurality of legs may be attached underneath the movable frame and may support the structure. The structure may be a mattress, and the movement of the movable frame may be controlled by at least one of a controller and a mobile application. At least one of the controller and the mobile application may adjust an intensity of the movement of the movable frame. At least one of the controller and the mobile application may control a time period that the movable frame may create the movement. At least one additional leg, in addition to the plurality of legs, may be arranged to provide greater support for the bed system.

Other technical features may be readily apparent to one skilled in the art from the following drawings, descriptions and claims.

BRIEF DESCRIPTION OF THE DRAWING

For a more complete understanding of this disclosure and its features, reference is now made to the following description, taken in conjunction with the accompanying drawing, in which:

The FIGURE depicts a bed frame system according to an embodiment of the present disclosure.

DETAILED DESCRIPTION

The present disclosure generally provides a bed frame system that may include a mechanism arranged to move a bed frame and a mattress in a motion that may simulate movement of a body of water in an embodiment of the present disclosure.

The FIGURE depicts bed frame system 100 that may provide movable frame 110 that may be arranged to support mattress 120 on a top of movable frame 110 according to an embodiment of the present disclosure. It should be appreciated that mattress 120 may be a standard mattress or may be a mattress configured for use on movable frame 110 in embodiments of the present disclosure. Mechanism 130 may be attached underneath movable frame 110 that may be in the form of an electrical and/or a mechanical device. Mechanism 130 may move movable frame 110 in an oscillatory motion that may mimic or simulate the movement of a body of water. It should be appreciated that bed frame system 100 may sway a user and cause the user to feel as though bed frame system 100 exhibits the movement of ocean water or another body of water.

Controller 140 may be connected to movable frame 110 and/or mechanism 130 and may be configured to allow the user to adjust functions of bed frame system 100. Controller 140 may be configured to adjust the intensity of movement provided by movable frame 110. Controller 140 may be configured to set and/or adjust a predetermined time period that movable frame 110 moves. For example, controller 140 may be configured to adjust a time period that movable frame 110 and mattress 120 move. Mobile application 150 may also adjust the time period that movable frame 110 and mattress 120 move. It should be appreciated that additional functions or properties of bed frame system 100 may be adjusted or controlled by controller 140. It should be appreciated that a low intensity of bed frame system 100 may barely move movable frame 110, and a high intensity of bed frame system 100 may actively move movable frame 110 in embodiments of the present disclosure.

Bed frame system 100 may communicate with mobile application 150 in an embodiment of the present disclosure. Mobile application 150 may be in communication with bed frame system 100 and may adjust an intensity of movement of movable frame 110. Bed frame system 100 may provide an electronic system that may be arranged in housing 160 that may be attached to movable frame 110. A ball and socket may be connected to movable frame 110 and may operate to move movable frame 110 and mattress 120. Bed frame system 100 may provide a plurality of legs that may be attached to movable frame 110. It should be appreciated that the plurality of legs may stabilize mattress 120 on top of movable frame 110. At least one additional leg may be included in addition to the plurality of legs and may provide greater structural support to bed frame system 100.

Movable frame 110 may receive structure 120 that may be made of a deformable material in an embodiment of the present disclosure. The deformable material may be placed on top of movable frame 110. It should be appreciated that structure 120 made of a deformable material may be a mattress in an embodiment of the present disclosure. Movable frame 110 may further provide electronic mechanism 130 that may be attached underneath movable frame 110. Electronic mechanism 130 may move movable frame 110 in a motion that may mimic or simulate the movement of a body of water. Movable frame 110 may provide a plurality of legs that may be attached underneath movable frame 110 and may support structure 120. Movable frame 110 or movement of movable frame 110 may be controlled by at least one controller 140 and/or by mobile application 150. Controller 140 may be configured to adjust the intensity of movement provided by movable frame 110. Controller 140 may be configured to set and/or adjust a predetermined time period that movable frame 110 moves. It should be appreciated that additional functions or properties of movable frame 110 may be adjusted or controlled by controller 140. It should be appreciated that a low intensity may barely move movable frame 110, and a high intensity may actively move movable frame 110 in embodiments of the present disclosure.

It should be appreciated that bed frame system 100 and movable frame 110 may eliminate movement of bed frame system 100, movable frame 110, and/or components thereof. It should further be appreciated that bed frame system 100 and movable frame 110 may oscillate, sway, provide sinusoidal motion, and/or rotate up to approximately 360 degrees or at other angles desired by the user. It should also be appreciated that bed frame system 100 and movable frame 110 may improve sleep and sleep patterns. It should be appreciated that bed frame system 100 may provide therapeutic, recovery, and health benefits.

It may be advantageous to set forth definitions of certain words and phrases used in this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A bed frame system comprising:
   a movable frame arranged to support a mattress provided on a top of the movable frame;
   a mechanism attached underneath the movable frame, the mechanism arranged to move the movable frame in an oscillatory motion similar to a motion of a body of water; and
   a controller configured to adjust an intensity of the movement caused by the mechanism and a time period the movable frame and the mattress move; and
   a mobile application in communication with the bed frame system to adjust the intensity of the movement caused by the mechanism and the time period the movable frame and the mattress move.

2. The bed frame system of claim 1, further comprising:
   a ball and socket arranged to move the movable frame and the mattress.

3. The bed frame system of claim 1 further comprising:
   an electronic system arranged in a housing attached to the movable frame.

4. The bed frame system of claim 1 further comprising:
   a plurality of legs attached to the frame to stabilize the mattress bed on top of the movable frame.

5. The bed frame system of claim 4 further comprising:
   at least one additional leg in addition to the plurality of legs arranged to provide greater support for the bed frame system.

6. A movable frame comprising:
   a structure made of a deformable material placed on a top of the movable frame;
   an electronic mechanism attached underneath the movable frame to create a movement of the movable frame mimicking a motion of a body of water, wherein the movement is to oscillate, sway, provide sinusoidal motion, and/or rotate the movable frame; and
   a plurality of legs attached underneath the movable frame to support the structure,
   wherein the movement of the movable frame is controlled by at least one of a controller and a mobile application, and
   wherein the at least one of the controller and the mobile application adjust an intensity of the movement of the movable frame and control a time period that the movable frame creates the movement.

7. The movable frame of claim 6, wherein the structure is a mattress.

8. The movable frame of claim 6 further comprising:
   at least one additional leg in addition to the plurality of legs arranged to provide greater support for the bed system.

\* \* \* \* \*